United States Patent [19]

Boulware

[11] Patent Number: 4,767,861

[45] Date of Patent: Aug. 30, 1988

[54] RECOVERY OF BENZO-C-PHENANTHRIDINE ALKALOIDS

[75] Inventor: Richard Boulware, Ft. Collins, Colo.

[73] Assignee: Vipont Laboratories, Fort Collins, Colo.

[21] Appl. No.: 81,704

[22] Filed: Aug. 4, 1987

Related U.S. Application Data

[63] Continuation of Ser. No. 822,967, Jan. 28, 1986, abandoned, which is a continuation of Ser. No. 596,589, Apr. 4, 1984, abandoned.

[51] Int. Cl.$^4$ .............. C07D 221/18; C07D 491/056; C07D 491/153
[52] U.S. Cl. ........................ 546/41; 546/48; 546/61; 424/195.1
[58] Field of Search ............................ 546/41, 48, 61; 424/195.1; 514/279, 280, 284, 285

[56] References Cited

U.S. PATENT DOCUMENTS

| | | | |
|---|---|---|---|
| 3,843,788 | 10/1974 | Iwasa et al. | 424/195 |
| 3,849,561 | 11/1974 | Iwasa et al. | 424/258 |
| 4,145,412 | 3/1979 | Ladanyi | 424/58 |
| 4,335,110 | 6/1982 | Collins | 424/145 |
| 4,376,115 | 3/1983 | McCrorey | 424/145 |
| 4,406,881 | 9/1983 | Ladanyi | 424/49 |

FOREIGN PATENT DOCUMENTS

| | | | |
|---|---|---|---|
| 2755577 | 6/1979 | Fed. Rep. of Germany | 546/41 |
| 2856577 | 6/1980 | Fed. Rep. of Germany | 546/41 |
| 0022355 | 7/1970 | Japan | 514/279 |
| 2078109 | 1/1982 | United Kingdom | 514/279 |
| 0495311 | 4/1976 | U.S.S.R. | 546/41 |
| 0931186 | 6/1982 | U.S.S.R. | 514/280 |

OTHER PUBLICATIONS

Mitscher, et al., Lloydia, vol. 41, No. 2, pp. 145–150 (3–4/1978).
Gheorghiu, et al., Chemical Abstracts, vol. 74, 110201b (1971).
Loyzuk, et al., Chemical Abstracts, vol. 87, 78524q (1977).
Vichkanova, et al., Chemical Abstracts, vol. 89, 100745c (1978).
Hladon, et al., Chemical Abstracts, vol. 92, 15307d (1980).

Primary Examiner—Donald G. Daus
Assistant Examiner—Diana G. Rivers
Attorney, Agent, or Firm—Eric P. Schellin

[57] ABSTRACT

A method for extracting benzo-c-phenanthridine alkaloids from plants of the families Papaveraceae Fumariaciae, and Berberidacae, comprising extracting ground plant material with acidulated methanol precipitating the extract with an acid salt which is soluble in methanol, redissolving the precipitated salt in water, adding sufficient acid to form a precipitate, and collecting the precipitate so formed. The benzo-c-phenanthridine alkaloids have valuable properties as antimicrobials as well as in treating mouth odors, gingivitis, and periodontitis.

5 Claims, No Drawings

RECOVERY OF BENZO-C-PHENANTHRIDINE ALKALOIDS

This application is a continuation of application Ser. No. 822,967, filed Jan. 28, 1986 which is a continuation of application Ser. No. 596,589, filed Apr. 4, 1984, both now abandoned.

BACKGROUND OF THE INVENTION

The present invention relates to a method for recovering active benzo-c-phenanthridine alkaloids from plants containing these compounds.

*Sanguinaria canadensis*, Linn (family Papvaraceae) is commonly known as Bloodroot, Redroot, Puccoon, Teterwort, etc., and is a perennial herb native to North America. The plant and its juices have been used for various purposes in pre-historical and historical times. The plant has been used, in particular, as a folk remedy. The plant has generally been used whole, either undried (fresh) or dried. The usual procedure is to powder the dried plant and mix it with a carrier. This folk remedy has been tried for such conditions as asthma, bronchitis, dysentery, ringworm and a substantial list of other ailments.

The rhizome of the plant has not been used much in modern times because Sanguinaria is a local irritant which in relatively mild does, up to toxic quantities, produces epigastric burning with vomiting, tormenting thirst, faintness, dimness of vision, vertigo, and alarming prostration. In doses of about one gram it is a violent emetic. The present principal use of Sanguinaria is as a stimulant expectorant in cough syrups and in homeopathic medicine.

An early patent, U.S. Pat. No. 209,331, discloses the use of bloodroot, zinc chloride, and kerosene oil in equal proportions for treating open sores. U.S. Pat. No. 433,257, describes a salve of pulverized bloodroot, armenian bole, powdered rosin, lard, and Stockholm tar for use in the treatment of piles. U.S. Pat. No. 2,344,830, discloses the use of a mixture of zinc chloride, stibnite, and bloodroot to fix and outline diseased tissue for excision by surgery.

More recently, it has been discovered that extracts of Sanguinaria and other plants of the families Papaveracease, Fumariaceae and Berberidaceae such as *Macleaya cordata, Corydalis sevctcozii, C. ledebouni, Bocconia frutescens, Argemone mexicanus* and *Chelidonium majus* contain benzo-c-phenanthridine alkaloids, which are believed to have valuable properties in conditioning oral tissue, as well as in preventing and treating gingivitis, periodontitis, and mouth odors. Several patents have disclosed the use of extracts of Sanguinaria for such purposes, notably U.S. Pat. Nos. 4,145,412; 4,376,115; 4,406,881;German Offen. No. 2,907,406; U.K. Pat. No. 2,042,336; Belgian Pat. No. 888,843. These patents describe the use of Sanguinaria extracts as antimicrobial agents as well as mouth treating agents.

The prior art cited above describes a method of extracting active ingredients from *Sanguinaria canadensis* by extracting cut or ground bloodroot with methanol for at least 24 hours at an elevated temperature, filtering the liquid extract obtained, evaporating the extract to dryness, dissolving the dried residue in chloroform, adjusting the chloroform solution to an acid pH by the addition of hydrochloric acid, filtering the acidified extract, evaporating it to dryness, and dissolving the dried residue in glycerine for mixing with a carrier.

SUMMARY OF THE INVENTION

The present invention is directed to a more refined method of obtaining a valuable extract from plants of the families Papaverucease, Fumariaceae, and Berberidaceae such as *Sanguinaria canadensis, Macleaya cordata, Corydalis sevctvozzii, C. ldedbouni, Argemone mexicanus, Chelidonium majus, Bocconia frutescens,* and mixtures thereof, which extract has been identified as a mixture of benzo-c-phenanthridine alkaloids.

The benzo-c-phananthridine alkaloids which have been identified in Sanguinaria include sanguinarine, chelirubine, sanguirubine, berberine, chelilutine, chelerythrine, and sanguilutine.

In the process of the present invention, the methanol extractant is acidified to a pH of 1 to 3. An acid salt is then used as a precipitating agent. These steps yield an improved product which has a high degree of purity and an acceptable yield.

DETAILED DESCRIPTION OF THE INVENTION

Example I

The extraction is performed in two phases. In phase one, 25 kg. of ground bloodroot plant is placed into an extraction vessel. Next, 37.5 liters of methanol which has been acidulated with 37.5 grams of citric acid and 375 ml. HCl is added to the vessel. The vessel is left to stand untouched for 16-24 hours, after which time 25 liters of the extract is pulled off by a vacuum pump running at about 150 mm Hg vacuum. At this point, another 25 liters of methanol acidulated with 25 grams of citric acid and 250 ml. HCl is added to the extraction vessel, and this is allowed to stand for 6-8 hours. Another 25 liters of extract are withdrawn and added to the 25 liters collected above. To this combined 50 liters is added 2 liters of 27% solution of zinc chloride in methanol or 27% zinc chloride in water. The precipitate thus formed is allowed to sit at room temperature for 16-18 hours. The precipitate is collected and dried in an oven set 70° C.

In phase 2, the dried precipitate from phase one is weighed and redissolved in enough of a 2.5% solution of citric acid to effect a concentration of 1 g of precipitate to 40 ml of solution. This suspension is heated to about 70° C. and filtered hot. The collected hot filtrate is then combined with enough NaCl (USP) to effect a concentration of about 36.8 grams NaCl to 100 ml filtrate. The precipitate thus formed is allowed to stand at room temperature for 16-18 hours. The precipitate is filtered and placed into an oven, set at 60° C., to dry or dried in vacuo. The dried precipitate is then ground, weighed, and packaged for further use.

Instead of zinc chloride in Phase 1, step three, other acid salts which are soluble in methanol can be used. Such salts include zinc sulfate, zinc iodide, zinc nitrate, and other zinc acid salts which are soluble in methanol.

Example II

Phase 1

One kg of bloodroot is extracted with 3.0 liters of acidulated methanol (1% HCl, 0.5% citric acid) for three days over dry sea sand and glass wool. The extract is forced, using vacuum or air pressure, into a separate container. Approximately two-thirds of the methanol is recovered in the transfer.

For every liter of extract transferred, 40 ml of an acidulated salt solution is added as a precipitating agent. The precipitated extract is digested for 27 hours and collected as a filter cake by vacuum filtration. The filter cake is approximately 25% solids and 75% methanol. This material is dried in wax paper-lined steel pans at 50° to 60° C. for 48 to 72 hours until dry and brittle. Once dry, this material is ground to a fine powder.

Phase 2

One kg of fine dry powder from Phase 1 and 50 grams of citric acid are dissolved as completely as possible in 20 liters of water.

This material is filtered to remove water insolubles (down to the 2-8 micron range), and the filtrate is collected into a vessel containing a precipitating agent such as sodium chloride. The collecting vessel must be frequently agitated. The precipitate so generated is left to digest overnight, and the precipitate is collected as a filter cake which is dried in wax paper-lined steel pans at 40° C. This drying step takes approximately 24 hours. The yield is about 50% of that obtained in Phase 1.

The dried extract can then be dissolved in a suitable carrier, such as glycerine, for incorporation into products for oral use such as mouthwash, toothpaste, and the like.

What is claimed is:

1. A method for extracting benzo-c-phenanthridine alkaloids from plants of the families Papaveraceae, Fumariaceae, and Berberidaceae, comprising
grinding the plant, extracting the ground plant with acidulated methanol, precipitating the extract with a zinc salt which is soluble in methanol, redissolving the precipitated salt in water, adding sufficient acid to from a precipitate, and collecting the precipitate so formed.

2. The method of claim 1 wherein the plants are selected from the group consisting of *Sanguinaria canadensis, Macleaya cordata, Corydalis sevtvozii, C. ledebouni, Bocconia frutescens,* and *Chelidonium majus.*

3. The method of claim 2 wherein the plant is *Sanguinaria canadensis.*

4. The method of claim 1 wherein the benzo-c-phenanthridine alkaloids are selected from the group consisting of sanguinarine, chelirubine, sanguirubine, chelilutine, chelerythrine, sanguilutine, and mixtures thereof.

5. The method of claim 1 wherein the acid salt is selected from the group consisting of zinc chloride, zinc sulfate, zinc iodide, and zinc nitrate.

* * * * *